United States Patent [19]

Parker

[11] 4,072,724

[45] Feb. 7, 1978

[54] PROCESS FOR PREPARING HINDERED ALKENYL PHENOLS

[75] Inventor: Dane K. Parker, Massillon, Ohio

[73] Assignee: The Goodyear Tire & Rubber Company, Akron, Ohio

[21] Appl. No.: 628,686

[22] Filed: Nov. 3, 1975

[51] Int. Cl.$^2$ .................. C07C 39/18; C07C 39/12
[52] U.S. Cl. .................. 260/624 B; 260/619 R; 260/623 H; 260/623 R
[58] Field of Search .......... 260/624 B, 619 R, 623 R, 260/623 D, , 590 R, 623 H

[56] References Cited

U.S. PATENT DOCUMENTS

| | | | |
|---|---|---|---|
| 2,576,161 | 11/1957 | Thompson | 260/623 R |
| 2,708,210 | 5/1955 | Sias | 260/623 R |
| 2,811,566 | 10/1957 | Bader | 260/624 B |

Primary Examiner—James O. Thomas, Jr.
Assistant Examiner—Werren B. Lone
Attorney, Agent, or Firm—F. W. Brunner; J. A. Rozmajzl

[57] ABSTRACT

Hindered alkenyl phenols, all of which can be used as antioxidants, and some of which can be used as monomers, can be prepared by the dehydrohalogenation of the α-haloalkyl phenol.

9 Claims, No Drawings

PROCESS FOR PREPARING HINDERED ALKENYL PHENOLS

This invention relates to a process of preparing hindered alkenyl phenols, particularly 2,6-di-tert-alkyl-4-vinylphenols.

Beta substituted hindered alkenyl phenols are described in U.S. Pat. No. 3,644,539 as antioxidants. The method of preparation described therein cannot be used for the preparation of unsubstituted or alpha substituted hindered alkenyl phenols. It is desirable that an efficient process be found to prepare both alpha and beta substituted hindered alkenyl phenols.

It is an object of the present invention to provide a process for preparing hindered alkenyl phenols. It is another object of the present invention to provide a process for producing 2,6-di-tert-alkyl-4-vinylphenols. Other objects will become apparent as the description proceeds.

The objects of the present invention are accomplished by reacting an α-haloalkyl phenol with a basic dehydrohalogenation agent to form a hindered alkenyl phenol. The α-haloalkyl phenol and hindered alkenyl phenol have the following structural formulae:

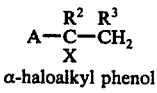   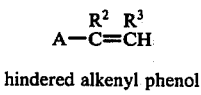

α-haloalkyl phenol    hindered alkenyl phenol wherein A has the structure

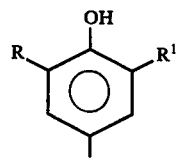

wherein R and R$^1$ are tertiary alkyl radicals having 4 to 12 carbon atoms, (preferably 4 to 8 carbon atoms) R$^2$ is selected from the group consisting of hydrogen and methyl, R$^3$ is selected from the group consisting of hydrogen, alkyl radicals having 1 to 6 carbon atoms, for example, methyl, and aryl radicals having 6 to 12 carbon atoms, for example, phenyl, with the proviso that at least one of R$^2$ and R$^3$ must be hydrogen, and X is a halo radical selected from the group consisting of chloro, bromo and iodo. Preferably R$^3$ is hydrogen and most preferably R$^2$ and R$^3$ are both hydrogen. Preferably X is chloro. Also preferably R and R$^1$ are tert.butyl radicals.

The objects of the present invention are also accomplished by the preparation of the α-haloalkyl phenol, which can be prepared from an alkyl phenol having the following structure

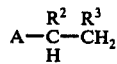

by reacting the alkyl phenol with a halogen such as Cl$_2$ to form the quinol halide which has the following structural formula:

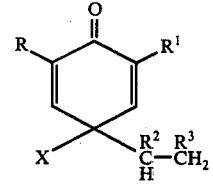

said quinol halide being rearranged to the α-haloalkyl phenol by treatment with aqueous HX, where X is selected from the group consisting of Cl, Br and I.

The α-haloalkyl phenol can also be prepared by reacting an alcohol having the following structure

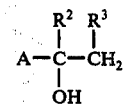

with HX. When R$^2$ is hydrogen, the alcohol can be prepared by reacting a hindered phenol having the structure

AH with an acid halide having the following structure

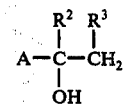

to form the ketone having the following structure

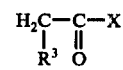

The ketone is reduced chemically or catalytically by known methods to form the above-identified alcohol where R$^2$ is hydrogen.

The alcohol can also be formed by reacting a hindered phenolic ketone or aldehyde with a Grignard reagent.

The dehydrohalogenation agents are well known in the art and are basic compounds such as, for example, tertiary amines such as pyridine, quinoline, triethylamine, tri-n-butylamine, or N,N-dimethyl aniline. The agent can also be an alkali metal hydroxide such as sodium or potassium hydroxide.

Where an alkali metal hydroxide is used, it must be somewhat soluble in the reaction medium used. For example, both sodium and potassium hydroxide can be used in ethanol. Most any non-aqueous medium can be used with due consideration being given to the standard solubility factors. The reaction medium can double as the dehalogenation agent. Pyridine, for example, is such a compound. Reaction temperatures can be determined routinely. As a guideline, but not as a limitation, alkali metal hydroxides such as potassium hydroxide are preferably used at the reflux temperature of the solvent, although reactions can be run at lower temperatures. A general, but not limiting, reaction temperature range is from 60° C. to 200° C.

When the quinol halide route is followed in the manufacture of the α-haloalkyl phenol, the alkyl phenol/halogen reaction is carried out in a solvent such as carbon tetrachloride. As guidelines, the reaction can be carried out at a temperature of −15° C. to 80° C., preferably from 0 to 10° C. Also as a guideline, the solvent should not be reactive with the halogen but should act as a solvent for it. Typical solvents are halogenated solvents such as tetrachloroethane, carbon tetrachloride, and the freons. The reaction is carried out in the presence of a tertiary amine such as pyridine to react with the HX formed. After the formation of the quinol halide, it is preferred that the pyridine and pyridien hydrohalide formed as a result of the reaction be extracted from the reaction mixture with water. Otherwise in the subsequent rearrangement step the catalyst HX will react with the pyridine instead of the quinol halide. A catalytic amount, for example, .001 to 1 part by weight per 100 parts by weight of the quinol halide, of aqueous hydrogen halide is added to the quinol halide and a rearrangement takes place to form the α-haloalkyl phenol. This reaction is not a strenuous one and may take place at room temperature.

When the α-haloalkyl phenol is prepared from the alcohol by way of reaction with aqueous HX, the alcohol is dissolved in a minimal amount of solvent, the solvent being immiscible with aqueous HX. The solvent is illustrated by but not limited to heptane, hexane, benzene and toluene. The HX is added in the form of an aqueous, preferably concentrated, solution. The reaction may be carried out at or below room temperature. Naturally higher temperatures can be used.

When the alcohol is prepared by the reaction of the hindered phenol with an acid halide (acylation reaction) followed by a reduction reaction, Friedel-Crafts catalysts of the Lewis acid type are used in the acylation step. Conventional reaction mediums such as nitrobenzene, CCl$_4$ or carbon disulfide are also used. When the ketone is reduced to the alcohol, it is only necessary that a portion of the ketone be soluble in the reaction medium. Tetrahydrofuran and 1,4-dioxane exemplify the solvent. The reaction is run under pressure and normally at a temperature of 80° C. to 180° C. It is a catalyzed hydrogenation reaction and any hydrogenation catalyst can be used, for example, see Morris Freifelder, "Practical Catalytic Hydrogenation", 1971. However, it has been found that a selected catalyst is most desirable, the catalyst being copper chromite minimizes hydrogenolysis of the alcohol. It is preferred that the ketone be isolated and purified before being reduced, even when the selected catalyst is used.

It should be noted that the process conditions earlier recited are only guidelines to aid in the practice of the present invention in obtaining optimum results. They are in no way to be construed to be limitations, since conditions can vary according to the specific reactants being used and other variables. Optimum conditions can be determined by routine experimentation.

All of the hindered alkenyl phenols prepared by the process of the present invention can be used as antioxidants in polymers such as natural rubber, butadiene/styrene rubbers and polypropylene. Those hindered alkenyl phenols where R$^3$ is hydrogen can also be polymerized alone or with other monomers in emulsion free radical polymerization systems to form polymeric antioxidants and/or selfstabilizing polymers.

The following equations illustrate various process steps described earlier herein.

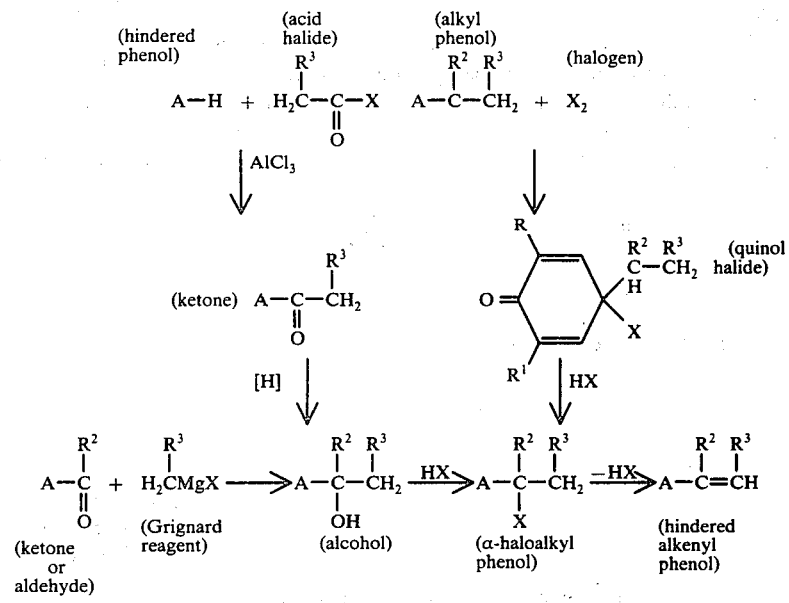

The following examples illustrate the preparation of substituted hindered alkenyl phenols by the process of the present invention and are not intended to limit the scope of the present invention.

EXAMPLE 1

Eight hundred milliliters of dry CCl$_4$ was cooled to 0° to 5° C. Anhydrous AlCl$_3$, 96.4 grams (0.70 mole) was added followed by the dropwise addition of 50 milliliters (0.70 mole) of acetyl chloride. After the addition of acetyl chloride was completed, 103 grams (0.50 mole) of 2,6-di-t-butylphenol dissolved in 100 milliliters of CCl$_4$ was added over a 1 hour period while maintaining a temperature below 10° C. The mixture was slowly warmed to room temperature and stirred an additional hour. The aluminum chloride/3,5-di-t-butyl-4-hydroxyacetophenone complex was hydrolyzed by pouring the reaction mixture into an excess of cold dilute hydrochloric acid. The lower CCl$_4$ layer was separated, and the solvent was evaporated to obtain 118 grams of 3,5-di-t-butyl-4-hydroxyacetophenone with a 95 percent yield and a melting point of 146 to 148° C. A high pressure autoclave was charged with 100 grams (.403 mole)

of 3,5-di-t-butyl-4-hydroxyacetophenone, 500 milliliters of dioxane and 10 grams of copper chromite catalyst. Pressure was raised to 1000 psi, and the mixture was heated to 125° to 135° C. until no more hydrogen was absorbed. The mixture was cooled, the catalyst filtered off and the solvent removed to obtain 96 grams of carbinol with a 95 percent yield and a melting point of 86° to 88° C. The carbinol was quantitatively converted to the 2,6-di-t-butyl-4-(α-chloro)ethylphenol by vigorous stirring of 50 grams (0.20 mole) of the carbinol dissolved in 100 milliliters of hexane with 100 milliliters of concentrated HCl for one hour at room temperature. The hexane layer was separated and the solvent removed. The residue was used in the final step. To the residue of 2,6-di-t-butyl-4-(α-chloro)ethylphenol was added 100 milliliters of pyridine. This solution was refluxed for 30 minutes. The pyridine was then removed by the vacuum distillation. The residue was washed thoroughly with water, then dissolved in a small amount of acetone and recrystallized at −78° C. to obtain 44 grams of 2,6-di-t-butyl-4-vinylphenol with a 95 percent yield of a melting point of 36 to 39° C.

EXAMPLE 2

A one-liter flask was charged with 46.8 grams (0.2 mole) of 2,6-di-t-butyl-4-ethylphenol, 40 milliliters of pyridine and 460 milliliters of $CCl_4$ and then cooled to 0 to 5° C. Chlorine, 9.1 milliliters at 0° to 5° C. (~0.2 mole) was slowly allowed to bubble under the surface of the reaction mixture. The chlorine was mixed with $N_2$ to aid a smooth evaporation. After addition of the $Cl_2$, the mixture was stirred five minutes at 0 to 5° C. and then 300 milliliters of cold water was added. The organic lower layer was separated and washed three times with 300 milliliter portions of water. Concentrated HBr (5 drops) was added and the mixture was shaken. The $CCl_4$ was removed at reduced pressure. Eighty milliliters of pyridine was added to the viscous yellow oil residue and the mixture was heated to reflux for one-half hour. The pyridine turned a dark redo-range. The mixture was allowed to stand overnight, and the excess pyridine was removed at reduced pressure. Three hundred milliliters of water and 60 milliliters of hexane were added. The mixture was shaken to dissolve the hydrochloride. The hexane takes up the product. The hexane layer was then washed twice with two (200 milliliter) portions of cold water. The hexane layer was separated and the hexane removed to obtain 43.48 grams of crude product. Theoretically 46.4 grams of product should be obtained. Gas chromatographic analysis indicated that the crude product consisted mostly (95 percent) of the desired compound and contained only a trace of the starting material. Distillation results in the recovery of 34.65 grams of the desired compound, i.e., a yield of 74.7 percent.

EXAMPLE 3

Example 2 was repeated substituting a bromine for chlorine. A yield of 62.5 percent was obtained based on 2,6-di-t-butyl-4-ethyl phenol consumed (69 percent based on the bromine used).

The following compounds illustrate, but do not limit, generic groups of compounds described earlier herein.

| Hindered Phenol |
| --- |
| 2,6-di-tert.-butylphenol |
| 2,6-di-tert.-pentylphenol |
| 2,6-di-tert.-hexylphenol |

| -continued |
| --- |
| 2,6-di-tert.-heptylphenol |
| Acid Halide |
| acetyl chloride |
| propionoyl chloride |
| butyroyl chloride |
| pentanoyl chloride |
| phenyl acetyl chloride |
| Alkyl Phenol |
| 2,6-di-tert.-butyl-4-ethylphenol |
| 2,6-di-tert.-butyl-4-isopropylphenol |
| 2,6-di-tert.-butyl-4-n-propylphenol |
| 2,6-di-tert.-butyl-4-n-butylphenol |
| 2,6-di-tert.-butyl-4-(β-phenethyl)phenol |
| Ketone |
| 3,5-di-tert.-butyl-4-hydroxyphenyl methyl ketone |
| 3,5-di-tert.-butyl-4-hydroxyphenyl ethyl ketone |
| 3,5-di-tert.-butyl-4-hydroxyphenyl propyl ketone |
| 3,5-di-tert.-butyl-4-hydroxyphenyl butyl ketone |
| 3,5-di-tert.-butyl-4-hydroxyphenyl benzyl ketone |
| Quinol Halide |
| 4-chloro-4-ethyl-2,6-di-tert.-butylcyclohexa-2,5-dienone |
| 4-bromo-4-isopropyl-2,6-di-tert.-butylcyclohexa-2,5-dienone |
| 4-chloro-4-n-butyl-2,6-di-tert.-butylcyclohexa-2,5-dienone |
| 4-chloro-4-(β-phenethyl)-2,6-di-tert.-butylcyclohexa-2,3-dienone |
| Aldehyde |
| 3,5-di-tert.-butyl-4-hydroxybenzaldehyde |
| 3,5-di-tert.-pentyl-4-hydroxybenzaldehyde |
| 3,5-di-tert-hexyl-4-hydroxybenzaldehyde |
| 3,5-di-tert.-octyl-4-hydroxybenzaldehyde |
| Grignard Reagent |
| methyl magnesium chloride |
| ethyl magnesium iodide |
| propyl magnesium bromide |
| n-butyl magnesium chloride |
| benzyl magnesium chloride |
| Alcohol |
| 1-(3,5-di-tert-butyl-4-hydroxyphenyl)ethanol |
| 1-(3,5-di-tert-butyl-4-hydroxyphenyl)propanol |
| 1-(3,5-di-tert-butyl-4-hydroxyphenyl)-1-methylethanol |
| 1-(3,5-di-tert-octyl-4-hydroxyphenyl)butanol |
| 1-(3,5-di-tert-butyl-4-hydroxyphenyl)β-phenethylol |
| α-Haloalkyl Phenol |
| 1-(3,5-di-tert-butyl-4-hydroxyphenyl)-1-chloroethane |
| 1-(3,5-di-tert-butyl-4-hydroxyphenyl)-1-bromopropane |
| 1-(3,5-di-tert-butyl-4-hydroxyphenyl)-1-chlorobutane |
| 2-(3,5-di-tert-octyl-4-hydroxyphenyl)-2-chloropropane |
| 1-(3,5-di-tert-butyl-4-hydroxyphenyl)-1-chloro-2-phenylethane |
| Hindered Alkenyl Phenol |
| 1-(3,5-di-tert-butyl-4-hydroxyphenyl)ethylene |
| 2-(3,5-di-tert-butyl-4-hydroxyphenyl)-1-propene |
| 1-(3,5-di-tert-butyl-4-hydroxyphenyl)-1-butene |
| 1-(3,5-di-tert-octyl-4-hydroxyphenyl)-1-pentene |
| 1-(3,5-di-tert-butyl-4-hydroxyphenyl)-2-phenylethylene |

While certain representative embodiments and details have been shown for the purpose of illustrating the invention, it will be apparent to those skilled in this art that various changes and modifications may be made therein without departing from the spirit or scope of the invention.

I claim:
1. A process of preparing a hindered alkenyl phenol comprising reacting (a) an α-haloalkyl phenol with (b) a basic dehydrohalogenation agent, wherein the α-haloalkyl phenol has the following structural formula

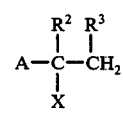

and the hindered alkenyl phenol has the following structural formula

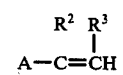

wherein A has the structure

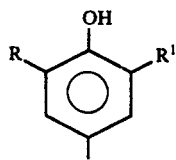

and wherein R and $R^1$ are tertiary alkyl radicals having 4 to 12 carbon atoms, $R^2$ is selected from the group consisting of hydrogen and methyl, $R^3$ is selected from the group consisting of hydrogen, alkyl radicals having 1 to 6 carbon atoms and aryl radicals having 6 to 12 carbon atoms, with the proviso that at least one of $R^2$ and $R^3$ is hydrogen, and X is a halo radical selected from the group consisting of chloro, bromo and iodo.

2. The process according to claim 1 wherein $R^3$ is hydrogen.

3. The process of claim 2 wherein $R^2$ is hydrogen, R and $R^1$ are tertiary butyl radicals and X is chloro.

4. The process of preparing a hindered alkenyl phenol from an α-haloalkyl phenol according to claim 1 comprising (a) reacting an alkyl phenol having the following structural formula

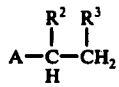

with a halogen selected from the group consisting of chlorine, bromine an iodine to form a quinol halide having the following structural formula

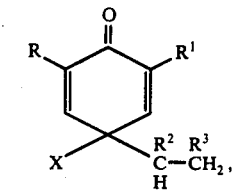

(b) treating the quinol halide with aqueous HX to form the α-haloalkyl phenol, and (c) reacting the α-haloalkyl phenol with the basic dehydrohalogenation agent.

5. A process of preparing a hindered alkenyl phenol from an α-haloalkyl phenol according to claim 1 wherein an alcohol having the following structure

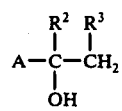

is reacted with HX to form the α-haloalkyl phenol.

6. A process according to claim 1 wherein $R^2$ is hydrogen and wherein the alcohol is prepared by reacting a hindered phenol having the structure AH with an acid halide having the structure

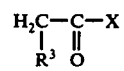

to form a ketone having the structure

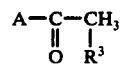

and reducing the ketone to said alcohol.

7. The process of claim 4 wherein the dehydrohalogenation agent is selected from the group consisting of basic tertiary amines and alkali metal hydroxides.

8. The process of claim 4 wherein the dehydrohalogenation agent is pyridine.

9. The process of claim 1 wherein the reaction occurs at a temperature of from 60° C. to 200° C.

* * * * *